United States Patent [19]

Kallimanis

[11] Patent Number: 4,857,554

[45] Date of Patent: Aug. 15, 1989

[54] METHOD FOR THE TREATMENT OF PSORIASIS

[76] Inventor: Georgios Kallimanis, 16, Proteos St., Athens, Greece

[21] Appl. No.: 85,757

[22] Filed: Aug. 17, 1987

[51] Int. Cl.[4] ............................................. A61K 31/19
[52] U.S. Cl. .................................... 514/557; 514/863
[58] Field of Search ......................................... 514/557

[56] References Cited

PUBLICATIONS

Chemical Abstracts 84:140591c, (1976).
Chemical Abstracts 84:160059r, (1976).
Merck Index, 9th Ed., #6673 & 9552, (1976).

*Primary Examiner*—Leonard Schenkman
*Attorney, Agent, or Firm*—Martin Smolowitz

[57] ABSTRACT

Psoriasis in humans is treated by applying to the affected skin area 2-6 times a day an ointment containing ursolic acid and oleanolic acid in the weight ratio of 3:1 dispersed in a vaseline/lanolin carrier. An homogenous ointment may be prepared by dissolving the acids in ethyl ether, adding the carrier, warming until homogeneous and heating to remove the ether.

2 Claims, No Drawings

METHOD FOR THE TREATMENT OF PSORIASIS

BACKGROUND OF THE INVENTION

Psoriasis is a chronic skin disease which progresses gradually, the main signs and symptoms of which are papulosquamous and itching. The present treatment of psoriasis is symptomatic and is based on the administration of steroids, antibiotics, keratolytics, antiseptics and in some cases cytostatic drugs. The treatment of posoriasis with the presently available drugs is considered satisfactory.

SUMMARY OF THE INVENTION

The present invention relates to an improved composition for the treatment of psoriasis based on a mixture of ursolic acid and oleanolic acid in a weight ratio of 3:1, dissolved in a petroleum jelly/lanolin carrier, preferably containing propyl paraben and methyl paraben as preservatives. The invention also relates to the method for preparation of the composition and the method of treatment of psoriasis with the composition.

DESCRIPTION OF PREFERRED EMBODIMENTS

The composition comprises (in parts by weight)

| | |
|---|---|
| Ursolic acid | 0.3–0.9 |
| Oleanolic acid | 0.1–0.3 |
| Petroleum jelly | 30–90 |
| Lanolin anhydrous and optionally | 10–30 |
| Propyl paraben | 0.02 |
| Methyl paraben | 0.005 |

The composition may be prepared as follows:

A mixture of the oleanolic and ursolic acids is dissolved in the necessary quantity of ethyl ether. A mixture of the lanolin/petroleum jelly is added to the ether solution which is then warmed in order to dissolve the ingredients and form a homogeneous mixture. To this mixture, the necessary quantity of methyl paraben and propyl paraben, dissolved in a small quantity of ethyl alcohol, is added. The whole is warmed to to remove the ether.

The above method is necessary only if a completely homogeneous mixture is desire. If not, the ingredients may be simply mixed and shaken well.

The obtained product is a yellow ointment having a slight odor like lanolin. It is stable under ambient conditions of temperature, moisture and light.

The composition according to the invention has been clinically tested on humans afflicted with psoriasis. Even after the first application of this ointment, the itching ceases and the rest of the symptoms subside.

After the first week of treatment, exfoliation and elimination of the psoriatic area occur and in psoriasis of recent onset, complete cure follows in about 70–80% of the cases. During the second week of treatment the recent cases of psoriasis are completely cured and the characteristic white spots are left in the psoriatic areas, which again subside in a few days. The chronic severe forms of psoriasis are cured in 50–60% of the cases. During the third week of treatment, the usual psoriasis cases are cured. The recommended dosage is 2–6 times daily according to the severity of the case. Continuous application of the above ointment for 4 months did not reveal any side effects. It is not necessary to combine this drug with any other.

The drug may be identified as follows:

0.1 g of the ointment is dissolved in 10 ml of ethyl ether. A small quantity is chromatographed in layer (silica gel layer 0.25 mm) using toluene:acetic acid:acetone 100:0.07:3 as the solvent. After the chromatography, the chromatogram is sprayed with a 20% solution of $SbCl_3$ in methanol and warmed to 100° C. Two characteristic blue spots are seen: the ursolic acid spot with Rf 0.065 and the oleanolic acid with Rf 0.125.

The above composition was used in the treatment of psoriasis on 40 patients of different age/sex distribution and duration of the disease. The clinical results are shown in the following table.

| | Patient's sex | Patient's age (in years) | Duration of disease (in years) | Distribution of Psoriasis | Duration of treatment (in days) |
|---|---|---|---|---|---|
| 1. | female | 30 | 7 | Upper-lower extremities | 20 |
| 2. | male | 43 | 28 | Whole body | 40 |
| 3. | male | 48 | 27 | Whole body | 42 |
| 4. | female | 12 | 1/12 | Upper-lower extremities | 12 |
| 5. | male | 74 | 8 | Elbows | 15 |
| 6. | female | 40 | 1 | Whole body | 15 |
| 7. | male | 66 | 43 | Lower extremities | 35 |
| 8. | male | 44 | 24 | Whole body | 45 |
| 9. | female | 38 | 1 | Hand extremities | 15 |
| 10. | male | 17 | 3 | Upper-lower extremities | 25 |
| 11. | male | 12 | 3 | " | 22 |
| 12. | female | 16 | 2 | " | 25 |
| 13. | female | 17 | 3 | " | 30 |
| 14. | male | 12 | 4 | Whole body | 35 |
| 15. | male | 14 | 9 | " | 40 |
| 16. | female | 12 | 4 | " | 40 |
| 17. | female | 50 | 10 | " | 45 |
| 18. | male | 64 | 30 | " | 60 |
| 19. | male | 50 | 30 | " | 40 |
| 20. | male | 75 | 10 | Hand extremities | 30 |
| 21. | female | 35 | 5 | " | 30 |
| 22. | male | 50 | 4 | Elbows | 35 |
| 23. | male | 18 | 5 | Whole body | 50 |
| 24. | male | 74 | 20 | Hand extremities | 30 |
| 25. | male | 52 | 22 | Whole body | 40 |
| 26. | male | 55 | 30 | " | 65 |
| 27. | male | 53 | 25 | " | 70 |
| 28. | male | 21 | 5 | " | 40 |
| 29. | male | 44 | 8 | Upper-lower extremities | 30 |
| 30. | male | 40 | 7 | " | 32 |
| 31. | male | 43 | 8 | " | 35 |
| 32. | female | 35 | 3 | Hand extremities | 25 |
| 33. | female | 55 | 20 | Whole body | 60 |
| 34. | female | 75 | 40 | Upper-lower extremities | 50 |
| 35. | male | 48 | 8 | Upper extremities | 45 |
| 36. | female | 45 | 5 | Upper-lower extremities | 30 |
| 37. | female | 65 | 10 | Feet | 20 |
| 38. | male | 12 | 2 | Whole body | 30 |
| 39. | female | 32 | 5 | " | 20 |
| 40. | male | 22 | 6 | " | 60 |

The above table reveals that this concentration of acids has therapeutic effects on psoriasis. Itching as well as other subjective symptoms cease completely from the first week of treatment.

After the first week of treatment one can see desquamation of psoriasis, diminution of the extent and heading of new forms of psoriasis in percentages up to 70–80%. During the second week of treatment the recent forms of psoriasis heal almost completely and in the sites of the rash, white patches remain which disappear within a few days. Grave chronic forms of psoriasis heal in percentages up to 50–60%. During the third week of treatment mild forms of psoriasis heal completely and the skin comes back to its normal condition.

Grave forms of psoriasis show a considerable improvement up to 60–70%. The rash becomes reddish and a regeneration of the skin is noticed.

Very serious whole body psoriatic patients show improvement within 40–70 days from the beginning of treatment.

The main characteristic qualities of the drug action are the ceasing of pruritus and the gradual disappearance of psoriatic lesicus.

A biopsy was done on a 74 year-old man on the 20th day of treatment and the result was as follows:

The microscopic examination of the spindle-shaped skin specimen was 2.5×1.0 cm in size and revealed a hyperkeratosis in the center, acanthosis and hyperkeratosis of the epidermis as well as lymphocytic inflammatory infiltrates around the vessels of the cutis. Perakeratosis or absence of the granulak stratum was not observed except in minimal foci. In the epidermis and close to the above few foci, few formations in the form of microabcesses of MUNRO and spongiotic vesicles of COGOJ were observed.

Summary

Restricted, focal, residual lesion of psoriasis.

Young subjects (under 16 years) compared to older individuals respond more rapidly to treatment.

The treatment in patients, who have been given cortisone treatment in the past, takes longer.

Two patients had a relapse of their psoriasis within 3 years during their aforementioned treatment, but this fact cannot be evaluated, because they stopped the therapy before the complete disappearance of the signs of psoriasis. After repeating their treatment they were completely cured.

The successful treatment of psoriasis is confirmed by biopsy, but since this procedure is usually objected to by the patients, it is recommended to continue the treatment 5 days after the complete disappearance of the symptoms.

The mechanism of the action of the composition, as well as the etiology of psoriasis are unknown.

I claim:

1. A method for the treatment of psoriasis on the skin of a human, comprising applying to said skin affected with psoriasis an ointment comprising 0.3–0.9 part by weight of ursolic acid, 0.1–0.3 part by weight of oleanolic acid, 30–90 parts by weight of petroleum jelly and 10–30 parts by weight of anhydrous lanolin in the weight ratio of ursolic acid to oleanolic acid of 3:1 at the rate of 2 to 6 times daily until the symptoms of psoriasis have disappeared.

2. The method according to claim 1, wherein the ointment further comprises 0.2 part by weight of propyl paraben and 0.005 part by weight of methyl paraben.

* * * * *